US00PP33165P2

(12) United States Plant Patent
Bak et al.

(10) Patent No.: US PP33,165 P2
(45) Date of Patent: Jun. 15, 2021

(54) ***GUZMANIA* PLANT NAMED 'DESIRE'**

(50) Latin Name: *Guzmania hybrida*
Varietal Denomination: DESIRE

(71) Applicant: Corn Bak B.V., Assendelft (NL)

(72) Inventors: Elly Bak, Rijsenhout (NL); Nicolaas D. M. Steur, Oude Niedorp (NL)

(73) Assignee: Corn Bak B.V.

( * ) Notice: Subject to any disclaimer, the term of this patent is extended or adjusted under 35 U.S.C. 154(b) by 0 days.

(21) Appl. No.: 16/868,251

(22) Filed: May 6, 2020

(51) Int. Cl.
*A01H 5/02* (2018.01)
*A01H 6/22* (2018.01)

(52) U.S. Cl.
USPC ..... Plt./371

(58) Field of Classification Search
USPC ..... Plt./371
CPC ... A01H 5/02; A01H 5/00; A01H 6/22; A01H 6/225; A01H 1/02
See application file for complete search history.

*Primary Examiner* — June Hwu
(74) *Attorney, Agent, or Firm* — Cassandra Bright

(57) ABSTRACT

A new and distinct cultivar of *Guzmania* plant named 'DESIRE' characterized by a solid growth habit; funnel-form rosette plant, measuring about 40 to 50 cm in height (above the pot when flowering), numerous green color foliage (measuring about 45 cm in length and about 4.0 to 4.5 cm in width), and superior floral bract production. Bracts have a unique yellow inflorescence (RHS 13A), compound inflorescence (measuring about 15 cm in height and about 20 cm in diameter), and long-lasting habit. The new variety is a *Guzmania*, typically produced as an indoor ornamental plant.

1 Drawing Sheet

Latin name of the genus: *Guzmania hybrida.*
Variety denomination: 'DESIRE'.

BACKGROUND OF THE INVENTION

The present invention relates to a new and distinct hybrid cultivar of *Guzmania* plant, botanically known as *Guzmania hybrida*, of the family Bromeliaceae, and hereinafter referred to as 'DESIRE'. *Guzmania* is native to tropical America. *Guzmania* is predominantly epiphytic with a few terrestrial species and is native to the tropics. For the most part, species vary in diameter from 7 or 8 inches to 3 or 4 feet and have rosettes of glossy, smooth-edged leaves. Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived. *Guzmania* may be advantageously grown as pot plants for greenhouse or home use. Typically, the plants are shaded from direct sunlight. During the spring to autumn period, the central vase-like part of the leaf rosette is normally filled with water.

The new *Guzmania* 'DESIRE' was discovered and selected by the inventors in a research greenhouse during 2011 as a single flowering plant in a controlled breeding program in Assendelft, The Netherlands. The new *Guzmania* 'DESIRE' originated from a naturally occurring mutation of *Guzmania* (hybrid) 'OSTARA' (unpatented).

Asexual reproduction of the new *Guzmania* cultivar was first performed by off-shoots beginning in 2017 and then by tissue culture beginning in 2018 in Assendelft, The Netherlands, with first flowering after asexual reproduction occurring in 2020 in Assendelft, The Netherlands. Asexual reproduction of the *Guzmania* 'DESIRE' has demonstrated that the combination of characteristics as herein disclosed for the new cultivar are firmly fixed and retained through successive generations of asexual reproduction. The new cultivar reproduces true to type.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey', Berlin (1986); and Rauh, Werner, BROMELIEN, Verlag Eugen Ulmer, Stuttgart (1981).

SUMMARY OF THE INVENTION

The following traits have been repeatedly observed and are determined to be unique characteristics of 'DESIRE' which in combination distinguish this *Guzmania* as a new and distinct cultivar:

1. Solid growth habit.
2. Funnel-form rosette plant, measuring about 40 to 50 cm in height (above the pot when flowering).
3. Numerous, green colored foliage, measuring about 45 cm in length and about 4.0 to 4.5 cm in width.
4. Superior floral bract production.
5. Unique yellow inflorescence (RHS Yellow 13A).
6. Compound inflorescence, measuring from about 15 cm in height and about 20 cm in diameter.
7. Long-lasting habit.

PARENTAL COMPARISON

Plants the new *Guzmania* hybrid 'DESIRE' are similar to plants of 'OSTARA' in many horticultural characteristics.

The new variety however produces yellow bracts whereas the parent variety produces orange-red bracts.

COMMERCIAL COMPARISON

Of the many commercial cultivars known to the present inventors, the most similar in comparison to the new *Guzmania* 'DESIRE' is the cultivar 'HILDA' (unpatented). In comparison to 'HILDA' the inflorescences, leaves and plant shape of 'DESIRE' are more compact.

BRIEF DESCRIPTION OF THE PHOTOGRAPH

The accompanying photograph illustrates the overall appearance of the new *Guzmania* hybrid 'DESIRE' showing the colors as true as is reasonably possible with colored reproductions of this type. Colors in the photograph may differ slightly from the color values cited in the detailed botanical description which accurately describes the color of 'DESIRE'. The accompanying figure illustrates a typical flowering plant of 'DESIRE', at 12 months of age from potting size.

DETAILED BOTANICAL DESCRIPTION

'DESIRE' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant. For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant. The aforementioned photographs, together with the following observations, measurements and values describe the new *Guzmania* 'DESIRE' as grown in a greenhouse in Assendelft, The Netherlands, under conditions which closely approximate those generally used in commercial practice. Plants of 'DESIRE' were grown in a greenhouse with day temperatures ranging from 20° C. to 28° C. and night temperatures ranging from 18° C. to 23° C. No artificial lighting or photoperiodic treatments were conducted, but plants of 'DESIRE' are forced into flowering. The following fertilizer is added when growing plants of 'DESIRE': 1 part nitrogen, 0.6 parts phosphor, 2 parts Kalium and 0.1 parts magnesium. Color references are made to The Royal Horticultural Society Colour Chart (R.H.S.), 2001 edition, except where general colors of ordinary significance are used. Color values were taken under daylight conditions in a greenhouse in Assendelft, The Netherlands. The age of the plants of 'DESIRE' described is about 17 weeks after flowering treatment.

Botanical Classification: *Guzmania hybrida.*

PLANT

Height: About 40 to 50 cm (when flowering).
Width: About 75 cm.
Shape: Funnel form rosette.
Growth habit: Stemless.
Plant vigor: Good.
Flowering season: A fully grown plant can flower year-round, starting 17 weeks after induction of natural light or through flowering treatment.
Cold tolerance: Frost tender. Temperatures below 5° C. may damage plants.
Fragrance: None.

FOLIAGE

Quantity: About 18 (depending on the size of the plant).
Size of leaf:
- *Length.*—About 45 cm (when flowering).
- *Width.*—About 4.0 to 4.5 cm.

Overall shape: Linear-lanceolate.
Apex shape: Acuminate.
Base shape: Strap-like around central axis. Sheath about 5 cm wide, colored near Green 137D.
Margin: Entire.
Texture (both surfaces): Smooth.
Orientation: Leaf blades arch continuously from base.
Color: Leaf color can vary somewhat depending on growing conditions.
- *Immature.*—Upper surface: RHS Green 137A. Under surface: RHS Green 137A.
- *Mature.*—Upper surface: RHS Green 137A. Under surface: RHS Green 137A.

Venation: Indistinguishable from leaf blade.
Anthocyanin at leaf base: Absent

INFLORESCENCE

Borne: Erect stalks.
Shape: Compound.
Size:
- *Length.*—About 15 cm.
- *Diameter.*—About 20 cm.

Time of bloom: A fully grown plant can produce an inflorescence containing about 60 flowers (depending on the size of the plants), and can bloom the whole year starting about 17 weeks after natural induction or through flowering treatment.
Duration of bloom: Each flower blooms one (1) day and the total blooming of the whole inflorescence is about 5 weeks.
Flowers: Not visible during anthesis.
Petals:
- *Number.*—3 per flower.
- *Length.*—About 6.0 cm.
- *Width.*—About 0.5 cm.
- *Overall shape.*—Ligulate.
- *Apex shape.*—Obtuse.
- *Base shape.*—Fused.
- *Color.*—Upper and Under surfaces: RHS Yellow 4D and Yellow-Orange 15A.

Sepals:
- *Number.*—3 per flower.
- *Length.*—About 3.5 cm.
- *Width.*—About 0.5 cm.
- *Overall shape.*—Ligulate.
- *Apex shape.*—Acute.
- *Base shape.*—Fused.

*Color*.—RHS Yellow 4D.

BRACTS

Scape bracts:
*Quantity*.—About 11.
*Arrangement*.—Alternate.
*Position*.—About middle third.
*Size*.—Length: About 27 cm (lowest) to about 18 cm (scape bracts positioned just below the primary bracts). Width: About 4.0 cm.
*Overall shape*.—Lanceolate.
*Apex shape*.—Acute.
*Base shape*.—Fused.
*Margin*.—Entire.
*Texture*.—Smooth.
*Color*.—Upper surface: RHS Green 137A with Yellow 13B. Scape bracts which are closer to the primary bracts show more Yellow 13B. Lowermost scape bracts are mainly Green 137A with base Yellow 13B. Mid-section scape bracts are Green 137A along approximately ⅓ of distance from apex and Yellow 13B on basal ⅔ section. Uppermost scape bracts are Yellow 13B with an apex of Green 137A. Under surface: RHS Green 137A with Yellow 13B. Scape bracts which are closer to the primary bracts show more Yellow 13B.

Floral bracts/primary bracts:
*Quantity*.—About 14.
*Arrangement*.—Alternate.
*Size*.—Length: About 13.5 cm (lowest) to about 8 cm (closest to top of plant). Width: About 3.0 cm.
*Overall shape*.—Lanceolate.
*Apex shape*.—Acute.
*Base shape*.—Fused.
*Margin*.—Entire.
*Texture*.—Smooth.
*Curvature*.—Moderate.
*Color*.—Upper and Under surfaces: RHS Yellow 13A.

REPRODUCTIVE ORGANS

Androecium:
*Stamen*.—Number: 6 per flower. Length: About 4.5 cm. Diameter: About 1 mm. Color: RHS Yellow 4D.
*Anther*.—Length: About 0.5 cm. Color: RHS Yellow 4D.
*Pollen*.—None.

Gynoecium:
*Pistil*.—Number: 1 per flower. Length: About 5.5 cm.
*Stigma*.—Shape: 3-parted. Width: About 3 mm. Color: Near RHS Yellow 9B.
*Style*.—Length: About 4.5 cm. Color: Near RHS Yellow 9B.
*Ovary*.—Position: Superior. Shape: Conical. Length: About 0.8 cm. Diameter: About 0.3 cm. Color: Near RHS Yellow-Green 150D.

OTHER CHARACTERISTICS

Seeds/fruit: Sterile hybrid, therefore, no seed or fruit produced.
Disease/pest resistance: No observations made.
Disease/pest susceptibility: No observations made.

What is claimed is:

1. A new and distinct cultivar of *Guzmania* plant named 'DESIRE' as herein illustrated and described.

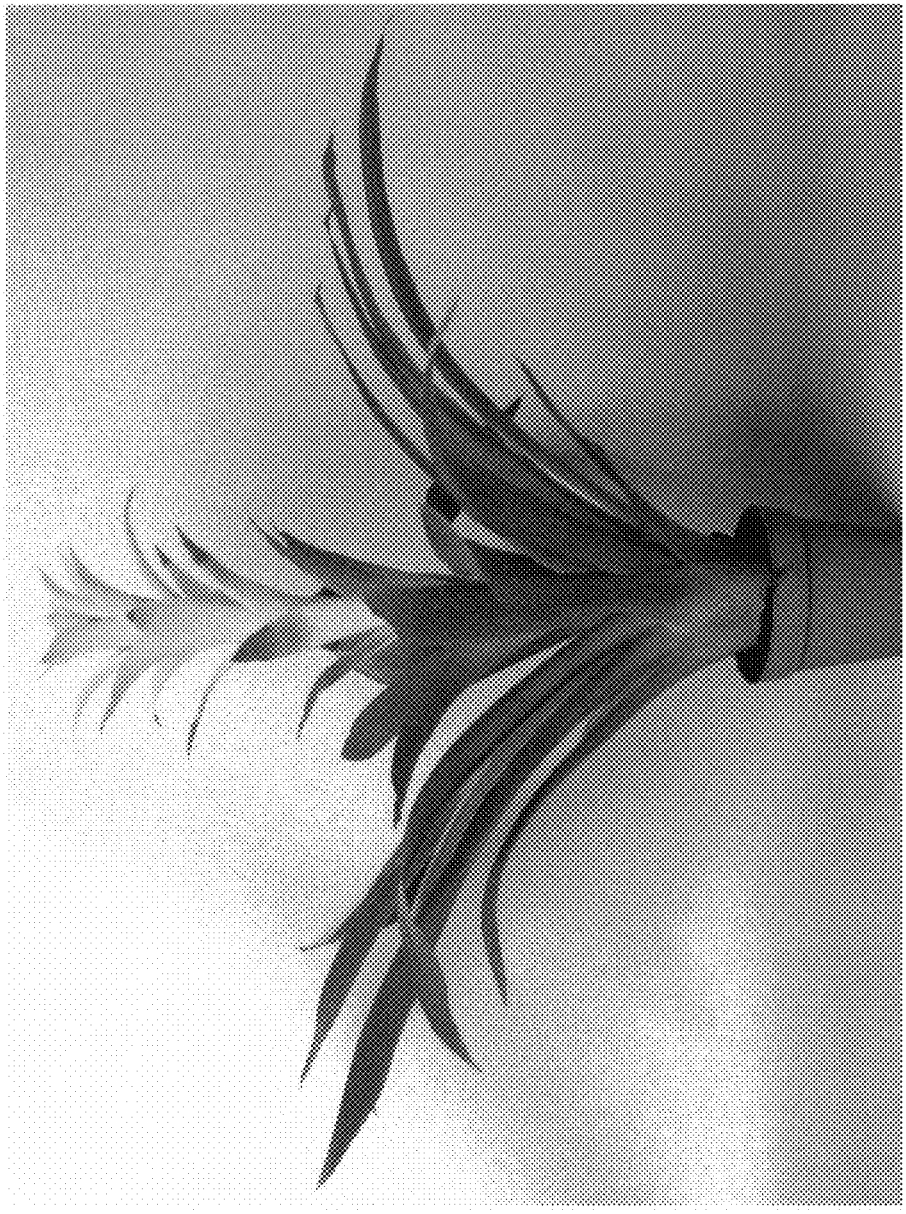

* * * * *